United States Patent [19]

Bonse et al.

[11] Patent Number: 5,093,343

[45] Date of Patent: Mar. 3, 1992

[54] SUBSTITUTED 1,3,4-OXA (THIA) DIAZOLINONES PROCESS FOR THEIR PREPARATION AND THEIR USE OF COMBATING ENDOPARASITES

[75] Inventors: Gerhard Bonse, Cologne; Nikolaus Müller, Monheim; Achim Harder, Leverkusen, all of Fed. Rep. of Germany

[73] Assignee: Bayer Aktiengesellschaft, Leverkusen, Fed. Rep. of Germany

[21] Appl. No.: 577,970

[22] Filed: Sep. 5, 1990

[30] Foreign Application Priority Data

Sep. 23, 1989 [DE] Fed. Rep. of Germany ....... 3931843

[51] Int. Cl.$^5$ .................... C07D 285/13; A01N 31/41
[52] U.S. Cl. .................................... 514/363; 548/142; 548/144
[58] Field of Search ................. 548/142, 144; 514/363

[56] References Cited

FOREIGN PATENT DOCUMENTS 2758765 3/1979 Fed. Rep. of Germany ...... 548/142

OTHER PUBLICATIONS

Pilgrim, J. Heterocyclic Chem. 19 (4) 823 (1982).

*Primary Examiner*—Robert Gerstl
*Attorney, Agent, or Firm*—Sprung, Horn, Kramer & Woods

[57] ABSTRACT

Substituted 1,3,4-oxa- and thiadiazolinones of the formula (I)

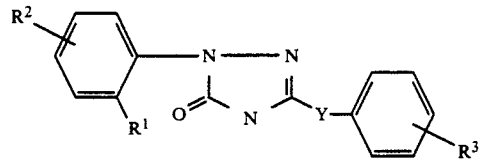

in which
$R^1$ represents hydrogen, alkyl, alkoxy, alkylthio, halogen, halogenoalkyl, halogenoalkoxy or halogenoalkylthio,
$R^2$ represents one or more identical or different radicals from among hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy or arylthio, which, in turn, can be sustituted,
$R^3$ represents one or more identical or different radicals from among hydrogen, alkyl, alkoxy, alkylthio, halogenoalkyl, halogenoalkoxy, halogenoalkylthio, alkylenedioxy, halogenoalkylenedioxy, halogen, CN, $NO_2$, alkylcarbonyl, carbalkoxy, alkylsulphonyl, arylsulphonyl, sulphamoyl, alkylsulphamoyl, dialkylsulphamoyl, aryl, aryloxy or arylthio, which, in turn, can be substituted,
X represents O or S, and
Y represents O or S,
with the exception of the compounds 5-phenoxy-3-(3,4-dichlorophenyl)-1,3,4-oxadiazol-2(3H)-one, and 5-phenoxy-3-(3-chloro-4-fluorophenyl)-1,3,4-oxadiazol-2-(3H)-one are disclosed as useful to combat endoparasites. Compositions containing these compounds and process for preparing them are also disclosed.

6 Claims, No Drawings

SUBSTITUTED 1,3,4-OXA (THIA) DIAZOLINONES PROCESS FOR THEIR PREPARATION AND THEIR USE OF COMBATING ENDOPARASITES

The present invention relates to new substituted 1,3,4-oxa(thia)diazolinones, process for their preparation, and their use for combating endoparasites.

Substituted 2-alkoxy-1,3,4-oxathiazolinones and their use against endoparasites are already known, but their actions are not always satisfactory (DE-OS (German Published Specification) 2,604,110). Previously described compounds are furthermore 2-aryloxy-1,3,4-oxadiazolinones (Pilgram, J. Heterocyclic Chem. 39, 823 (1982)); however, nothing is known about their use for combating endoparasites.

The present invention relates to substituted 1,3,4-oxa- and thiadiazolinones of the formula (I)

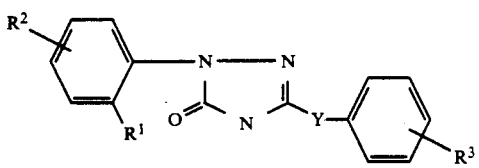

in which
$R^1$ represents hydrogen, alkyl, alkoxy, alkylthio, halogen, halogenoalkyl, halogenoalkoxy or halogenoalkylthio,
$R^2$ represents one or more identical or different radicals from amongst hydrogen, alkyl, alkoxy, alkylthio, halogenoalkyl, halogenoalkoxy, halogeno-alkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkyl-sulphamoyl, aryl, aryloxy or arylthio, which, in turn, can be substituted,
$R^3$ represents one or more identical or different radicals from amongst hydrogen, alkyl, alkoxy, alkylthio, halogenoalkyl, halogenoalkoxy, halogeno-alkylthio, alkylenedioxy, halogenoalkylenedioxy, halogen, CN, $NO_2$, alkylcarbonyl, carbalkoxy, alkyl-sulphonyl, arylsulphonyl, sulphamoyl, alkyl-sulphamoyl, dialkylsulphamoyl, aryl, aryloxy or arylthio, which, in turn, can be substituted,
X represents O or S, and
Y represents O or S,
with the exception of the compounds 5-phenoxy-3-(3,4-dichlorophenyl)-1,3,4-oxadiazol-2(3H)-one and 5-phenoxy-(3-chloro-4-fluorophenyl)-1,3,4-oxadiazol-2-(3H)-one.

The invention also relates to a process for the preparation of the new substituted 1,3,4-oxa- and thiadiazolinones of the formula

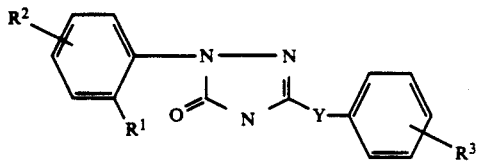

in which
$R^1$ represents hydrogen, alkyl, alkoxy, alkylthio, halogen, halogenoalkyl, halogenoalkoxy or halogenoalkylthio,
$R^2$ represents one or more identical or different radicals from amongst hydrogen, alkyl, alkoxy, alkylthio, halogenoalkyl, halogenoalkoxy, halogeno-alkylthio, alkylenedioxy, halogenoalkylenedioxy, halogen, CN, $NO_2$, $NH_2$, alkylamino, dialkylamino, alkylcarbonyl, carbalkoxy, alkylsulphonyl, aryl-sulphonyl, sulphamoyl, alkylsulphamoyl, dialkyl-sulphamoyl, aryl, aryloxy or arylthio, which, in turn, can be substituted,
$R^3$ represents one or more identical or different radicals from amongst hydrogen, alkyl, alkoxy, alkylthio, halogenoalkyl, halogenoalkoxy, halogeno-alkylthio, alkylenedioxy, halogenoalkylenedioxy, halogen, CN, $NO_2$, alkylcarbonyl, carbalkoxy, alkyl-sulphonyl, arylsulphonyl, sulphamoyl, alkyl-sulphamoyl, dialkylsulphamoyl, aryl, aryloxy or arylthio, which, in turn, can be substituted,
X represents O or S, and
Y represents O or S,
with the exception of the compounds 5-phenoxy-3-(3,4-dichlorophenyl)-1,3,4-oxadiazol-2(3H)-one and 5-phenoxy-3-(3-chloro-4-fluorophenyl)-1,3,4-oxadiazol-2-(3H)-one, characterized in that compounds of the formula (II)

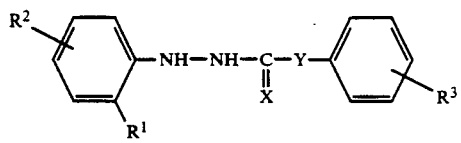

in which X, Y, $R^1$, $R^2$ and $R^3$ have the abovementioned meaning, are reacted with carbonylation reagents such as phosgene, phosgene or triphosgene, and the compounds obtained in this process, of the formula III

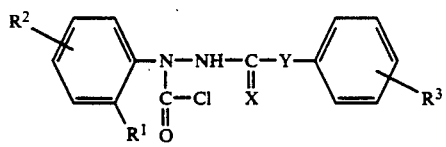

in which X, Y, $R^1$, $R^2$ and $R^3$ have the abovementioned meaning, are cyclized in the presence of bases.

The compounds of the formula I are outstandingly suitable for combating endoparasites, in particular in the field of veterinary medicine.

Preferred compounds of the formula I are those in which
$R^1$ represents halogen, preferably fluorine, chlorine, bromine or iodine; or represents alkyl having preferably 1 to 4, in particular 1 or 2, carbon atoms, such as methyl, ethyl, n.- and i.-propyl and n.-, i.-, s.- and t.-butyl; alkoxy having preferably 1 to 4, in particular 1 or 2, carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s.- and t.-butylthio; halogenoalkyl having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethyl, fluoro- or chloroethyl; halogeno-alkoxy having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethoxy; halogenoalkylthio having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethylthio, $R^2$ represents hydrogen, alkyl having preferably 1 to 4, in particular 1 or 2, carbon atoms, such as methyl, ethyl, n.- and i.-propyl and n.-, i.-, s.- and t.-butyl; alkoxy having preferably 1 to 4, in particular 1 or 2, carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s.-and t.-butylthio; halogenoalkyl having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethyl or fluoro- or chloroethyl; halogenoalkoxy having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethoxy; halogenoalkylthio having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethylthio; in the case of phenyl, $R^2$ represents alkylenedioxy having preferably 1 or 2 carbon atoms, such as methylenedioxy or ethylenedioxy; in the case of phenyl, $R^2$ represents halogen-substituted alkylene-dioxy having preferably 1 or 2 carbon atoms and preferably 1 to 4, in particular 2 to 3, halogen atoms, the halogen atoms being identical or different and preferably being fluorine or chlorine, in particular fluorine, such as difluoromethyl-enedioxy, trifluoroethylenedioxy or tetrafluoro-ethylenedioxy. Other substituents are halogen, preferably fluorine, chlorine, bromine and iodine, in particular chlorine and bromine; cyano; nitro; dialkylamino having preferably 1 to 4, in particular 1 or 2, carbon atoms per alkyl group, such as dimethylamino, diethylamino or methyl-n.-butylamino; alkylcarbonyl having preferably 2-4 carbon atoms; carbalkoxy having preferably 2 to 4, in particular 2 or 3, carbon atoms, such as carbomethoxy and carboethoxy; alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl; or represents phenyl, naphthyl, phenoxy, naphthoxy, phenylthio or naphthylthio, which, in turn, can be substituted, $R^3$ represents alkyl having preferably 1 to 4, in particular 1 or 2 carbon atoms, such as methyl, ethyl, n.- and i.-propyl and n.-, i.-, s.- and t.-butyl; alkoxy having preferably 1 to 4, in particular 1 or 2, carbon atoms, such as methoxy, ethoxy, n.- and i.-propyloxy and n.-, i.-, s.- and t.-butyloxy; alkylthio having preferably 1 to 4, in particular 1 or 2, carbon atoms, such as methylthio, ethylthio, n.- and i.-propylthio and n.-, i.-, s.-and t.-butylthio; halogenoalkyl having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as trifluoromethyl or fluoro- or chloroethyl; halogenoalkoxy having preferably 1 to 4, in particular 1 or 2, carbon atoms and preferably 1 to 5, in particular 1 to 3, halogen atoms, the halogen atoms being identical or different and preferably being fluorine, chlorine or bromine, in particular fluorine, such as tri-fluoromethoxy; halogenoalkylthio having preferably 1 to 4, in particular or 2, carbon atoms and preferably 1 to 5, in particular 1 to 3, halogen atoms, the halogen atoms being identical or different and preferably being fluorine, chlorine or bromine, in particular fluorine, such as trifluoromethylthio; in the case of phenyl, $R^3$ represents alkylenedioxy having preferably 1 or 2 carbon atoms, such as methylenedioxy or ethylenedioxy; in the case of phenyl, $R^3$ represents halogen-substituted alkyl-enedioxy having preferably 1 or 2 carbon atoms and preferably 1 to 4, in particular 2 to 3, halogen atoms, the haiogen atoms being identical or different and preferably being fluorine or chlorine, in particular fluorine, such as difluoromethyl-enedioxy, trifluoroethylenedioxy or tetrafluoro-ethylenedioxy. Other substituents are halogen, preferably fluorine, chlorine, bromine and iodine, in particular chlorine and bromine; cyano; nitro; alkylcarbonyl having preferably 2–4 carbon atoms; carbalkoxy having preferably 2 to 4, in particular 2 or 3, carbon atoms, such as carbomethoxy and carboethoxy; alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl; or represents phenyl, naphthyl, phenoxy, naphthoxy, phenylthio or naphthylthio, which, in turn, can be substituted, X represents O or S, and Y represents O or S.

Particularly preferred compounds of the formula I are those in which $R^1$ represents halogen, in particular chlorine or fluorine, $C_1$–$C_4$-alkyl, such as methyl, ethyl, $C_{1-4}$-alkoxy, such as methoxy or ethoxy, $C_{1-4}$-halogeno-aloxy, such as trifluoromethoxy, or $C_{1-4}$-halogeno-alkythio, such as trifluoromethylthio, $R^2$ represents halogen, in particular chlorine, fluorine or bromine, $C_{1-C4}$-alkyl, such as methyl, ethyl, $C_{1-4}$-aloxy, such as methoxy or ethoxy, $C_{1-4}$-halogeno-aloxy, such as trifluoromethoxy, $C_{1-4}$-halogenoalkyl-thio, such as trifluoromethylthio, or nitro or cyano; carbalkoxy, such as carbomethoxy and carboethoxy; alkylsulphonyl, such as methylsulphonyl and ethylsulphonyl, $R^3$ represents halogen, in particular chlorine, fluorine or bromine, $C_1$–$C_4$-alkyl, such as methyl or ethyl, $C_{1-4}$-alkoxy, such as methoxy or ethoxy, $C_{1-4}$-halogenoalkoxy, such as trifluoromethoxy, $C_{1-4}$-halogenoalkyl-thio, such as trifluoromethylthio, or nitro or cyano; carbalkoxy, such as carbomethoxy and carboethoxy; alkylsulphonyl, such as methylsulphonyl and ethylsulphonyl, X represents O or S, and Y represents O or S.

Very particularly preferred compounds of the formula I are those in which $R^1$ represents halogen, in particular fluorine, chlorine, $NO_2$, $CH_3$, or $CF_3$, $R^2$ represents halogen, in particular fluorine, chlorine, bromine, $CH_3$, $OCH_3$, $NO_2$ or CN, $R^3$ represents halogen, in particular fluorine, chlorine, bromine, $CH_3$, $OCH_3$, $NO_2$ or CN, X represents O, and Y represents O.

The following compounds of the formula (I) in which the radicals $R^1$, $R^2$, $R^3$, X and Y have the given meaning, may be mentioned individually.

| $R^1$ | $R^2$ | $R^3$ | X | Y |
|---|---|---|---|---|
| —Cl | —H | -4-Cl | O | O |
| —Cl | 3-CH$_3$ | —H | O | O |
| —H | —4Br | —H | O | O |
| —CH$_3$ | -3-CH$_3$ | —H | O | O |
| —CH$_3$ | -3-CH$_3$ | -4-Cl | O | O |
| —CH$_3$ | 3-Cl | —H | O | O |
| —Cl | -4-Cl | -4-Cl | O | O |
| —Cl | -3-CH$_3$ | -4-Cl | O | O |
| —H | 3,4-Cl$_2$ | —H | O | O |
| —F | -5-F | 4-CH$_3$ | O | O |
| —F | -6-F | —H | O | O |
| —Cl | 4,6-Cl$_2$ | —H | O | O |
| —Br | —H | —H | O | O |
| —OCH$_3$ | -4-Cl | -4-Cl | O | O |
| —Cl | —H | 4-CH$_3$ | O | O |
| —CH$_3$ | -4-CH$_3$ | —H | O | O |
| —Cl | 6-Cl | -4-Cl | O | O |
| -2-SCF$_3$ | —H | —H | O | O |
| —CH$_3$ | -3,4-CH$_3$ | -4-Cl | O | O |
| —Cl | —H | —H | S | S |
| —H | 3,4-Cl$_2$ | -4-Cl | S | S |
| —CH$_3$ | -3-CH$_3$ | —H | S | S |
| —CH$_3$ | -3-CH$_3$ | -4-CH$_3$ | S | S |
| —Cl | -3-Cl | —H | S | S |
| —Cl | 6-Cl | —H | S | S |
| —F | —H | —H | S | S |
| —H | 4-Br | -4-Cl | S | S |
| —OCH$_3$ | -4-Cl | —H | O | S |
| —Cl | -3-Cl | -3-Cl | S | S |
| —F | -6-F | —H | O | S |
| —Br | —H | —H | S | O |
| —Cl | -3-CH$_3$ | —H | S | O |
| —Cl | —H | —H | S | O |
| —CH$_3$ | -3-CH$_3$ | —H | S | O |
| —Cl | —H | -4-Cl | S | O |
| —CH$_3$ | —3CH$_3$ | -3-Cl | S | O |
| —F | 5-F | 4-Cl | S | O |
| —CH$_3$ | —CH$_3$ | 4-CH$_3$ | S | O |
| —Cl | —H | -4-CH$_3$ | S | O |
| —Cl | -4-CH$_3$ | -4-CH$_3$ | S | O |

If, in the preparation, phenyl 2-(2-chloro-phenyl)-hyrazinecarboxylate is employed as the compound of the formula (II) and phosgene as the carbonylation reagent, the process can be represented by the following equation:

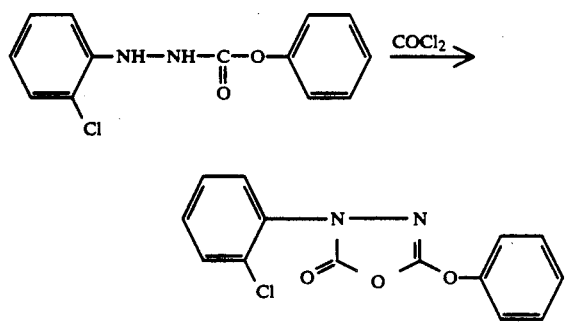

It is preferred to employ compounds of the formula II in which $R^1$, $R^2$, $R^3$, X and Y have the meanings indicated in the compounds of the formula (I) as being preferred.

The following compounds of the formula (II) may be mentioned individually: 4-chlorophenyl 2-(2-chlorophenyl)-hyrazinecarboxylate, phenyl 2-(2,3-dimethylphenyl)-hydrazinecarboxylate, 4-bromophenyl 2-(2,5-difluophenyl)-hydrazinecarboxylate, phenyl 2-(2-chloro-3-methyl)-hydrazinecarboxylate, 4-chlorophenyl 2-(2,4-dimethyl(phenyl)-hydrazinecarboxylate, phenyl 2-(2-chlorophenyl)-hydrazinedithiocarboxylate, 4-chlorophenyl 2-(2,3-dimethylphenyl)-hydrazinedithiocarboxylate, chlorophenyl 2-(4-bromophenyl)-hydrazinedithiocarboxy-late, phenyl 2-(o-tolyl)-hydrazinedithiocarboxylate, 4-nitrophenyl 2-(2-chlorophenyl)-hydrazinedithiocarboxy-late, 4-chlorophenyl 2-(2,3-dimethylphenyl)-hydrazine-thionocarboxylate, phenyl 2-phenylhydrazinecarboxylate p-tolyl 2-(2,5-difluorophenyl)hydrazinecarboxylate, 2-(2-methoxyphenyl)-hydrazinethiono p-tolyl ester, phenyl 2-(2-chlorophenyl)-hydrazinethiocarboxylate, 4-chloro-pheny-2-(2,3-dimethylphenyl)-helrazinethiocarboxylate and phenyl 2-(2,5-difluorophenyl)-hydrazinethiocarboxylate.

Some of the compounds of the formula (II) are known or can be prepared by processes known per se (Pilgram, J. Heterocyclic Chem. 39,823 (1982); US-P 3,395,234).

The reaction is carried out at temperatures from 20°–200° C., preferably at 50°–150° C., particularly preferably at the boiling point of the diluent.

Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, moreover esters, such as methyl acetate and ethyl acetate, furthermore nitriles, such as, for example, acetonitrile and propionitrile, benzonitrile or glutarodinitrile, and in addition amides, such as, for example, dimethylformamide, dimethylacetamide and N-methylpyrrolidone, and dimethyl sulphoxide, tetramethylene sulphone and hexamethylphosphoric acid triamide.

Suitable bases are inorganic and organic bases. Bases which may be mentioned are the hydroxides, carbonates, hydrogen carbonates and alcoholates of alkali metals and alkaline earth metals, furthermore amines, such as, in particular, tertiary amines, for example trimethylamine, triethylamine, N-methylmorpholine, pyridine, picolines, N-ethylpyrrolidine, diazabicyclo-(4,3,0)undecene (DBU), 1,4-diazabicyclo(2,2,2)octane (DABCO), diazabicyclo(3,2,0)nonene (DBN) and ethyl-diisopropylamine.

The compounds of the formulae II and the bases are employed in a ratio of 1:1 to 1:1.5 to each other. An approximately equimolar ratio is preferred.

When the reaction is complete, the diluent is partly distilled off (about 50%), aqueous acid is added to the remainder, and the compounds of the formula I are isolated in a manner known per se by extracting them with a suitable solvent, for example ether or methylene chloride. The compounds of the formula I can subsequently be purified in a customary manner, for example by chromatography.

The active compounds have a favorable toxicity to homothermals and are suitable for combating pathogenic endoparasites which occur in humans and in animal keeping and animal husbandry in livestock, breeding animals, zoo animals, laboratory animals, test animals and pets. They are active against all or individual stages of development of the pests as well as against resistant and normally-sensitive species. By combating the pathogenic endoparasites it is intended to reduce disease, deaths and reductions in productivity (for example in the production of meat, milk, wool, hides, eggs, honey etc.) so that more economical and simpler animal keeping is possible by using the active compounds. The pathogenic endoparasites include cestodes, trematodes, nematodes and acantocephala, in particular:

From the order of the Pseudophyllidea, for example Diphyllobothrium spp., Spirometra spp., Schistocephalus spp., Ligula spp., Bothridium spp., Dipllogonoporus spp..

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp..

From the order of the Enoplida, for example Trichuris spp., Capillaria spp., Trichomosoides spp., Trichinella spp..

From the order of the Rhabditia, for example Micronema spp., Strongyloides spp..

From the order of the Strongylida, for example Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp..

From the order of the Ascaridia, for example Ascaris spp., Toxascaris spp., Toxocara spp., Parascaris spp., Anisakis spp., Ascaridia spp..

From the order of the Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp..

The livestock and breeding animals include mammals such as, for example, cattle, horses, sheep, pigs, goats, camels, water buffaloes, donkeys, rabbits, fallow deer, reindeer, fur-bearing animals, such as, for example, minks, chinchilla and racoon, birds, such as, for example, chickens, geese, turkeys and ducks, fresh water and sea fish, such as, for example, trout, carps and eels, reptiles, and insects such as, for example, the honeybee and the silkworm.

The laboratory and experimental animals include mice, rats, guinea pigs, hamsters, dogs and cats.

The pets include dogs and cats.

The application can be both prophylactic and therapeutic.

The active compounds are used directly or in the form of suitable preparations enterally, parenterally, dermally, nasally, by treating the environment, or with the aid of shaped articles containing active compound, such as, for example, strips, plates, ribbons, collars, ear tags, limb bands or marking devices.

Enteral administration of the active compounds is effected for example orally in the form of powders, tablets, capsules, pastes, drinks, granules, orally applicable solutions, suspensions and emulsions, boli, medicated feed or drinking water. Dermal administration is effected for example in the form of dipping, spraying, pouring-on and spotting-on. Parenteral administration is effected for example in the form of injection (intramuscularly, subcutaneously, intravenously or intraperitoneally) or by implants.

The following are suitable preparations:

Solutions, such as solutions for injection, oral solutions, concentrates for oral administration after dilution, solutions for use on the skin or in body cavities, pour-on formulations or gels;

emulsions and suspension for oral or dermal administration and for injection; semi-solid preparations;

formulations in which the active compound is incorporated into an ointment base or into an oil-in-water or water-in-oil emulsion base;

solid preparations, such as powders, premixes or concentrates, granules, pellets, tablets, boli or capsules; aerosols and inhalants, shaped articles containing active compound.

Solutions for injection are administered intravenously, intramuscularly and subcutaneously.

Solutions for injection are prepared by dissolving the active compound in a suitable solvent and, if appropriate, adding additives, such as solubilizers, acids, bases, buffer salts, antioxidants or preservatives. The solutions are sterile filtered and filled in containers.

Solvents which may be mentioned are: physiologically acceptable solvents, such as water, alcohols, such as ethanol, butanol, benzyl alcohol, glycerol, propylene glycol, polyethylene glycols, N-methyl-pyrrolidone, and their mixtures.

If required, the active compounds can also be dissolved in physiologically acceptable vegetable or synthetic oils which are suitable for injection.

Solubilizers which may be mentioned are solvents which enhance the dissolution of the active compound in the main solvent or which prevent its precipitation. Examples are polyvinyl pyrrolidone, polyoxyethylated castor oil or polyoxyethylated sorbitan esters.

Preservatives are: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, a sterile procedure not being necessary.

Solutions for use on the skin are applied dropwise, spread on, rubbed in, splashed on or sprayed on. These solutions are prepared as described above in the case of solutions for injection.

It can be advantageous to add thickeners in the preparation. Thickeners are inorganic thickeners, such as bentonites, colloidal silica or aluminium monostearate, and organic thickeners, such as cellulose derivatives, polyvinyl alcohols and their copolymers, and acrylates and metacrylates.

Gels are applied to the skin or spread on or introduced into body cavities. Gels are prepared by adding such an amount of thickener to solutions which have been prepared as described above in the case of the solutions for injection, that a clear composition having an ointment-like consistency is formed. The thickeners used are the thickeners indicated further above.

Pour-on formulations are poured or splashed onto limited areas of the skin, the active compound penetrating the skin and acting systemically.

Pour-on formulations are prepared by dissolving, suspending or emulsifying the active compound in suitable solvents or solvent mixtures which are tolerated by the skin. If required, other auxiliaries, such as colorants, resorption accelerators, antioxidants, agents which impart protection against light or tackifiers are added.

Solvents which may be mentioned are: water, alkanols, glycols, polyethylene glycols, polypropylene glycols, glycerol, aromatic alcohols such as benzyl alcohol, phenylethanol or phenoxyethanol, or esters such as acetic ester, butyl acetate or benzyl benzoate, ethers such as alkylene glycol alkyl ethers such as dipropylene glycol monomethyl ether or diethylene glycol monobutyl ether, ketones, such as acetone or methyl ethyl ketone, aromatic and/or aliphatic hydrocarbons, vegetable or synthetic oils, DMF, dimethylacetamide, N-methylpyrrolidone or 2,2-dimethyl-4-oxy-methylene-1,3-dioxolane.

Colorants are all colorants which are released for use in animals, and they can be dissolved or suspended.

Resorption accelerators are, for example, DMSO, spreading oils such as isopropyl myristate, dipropylene glycol pelargonate, silicone oils, fatty acid esters, triglycerides or fatty alcohols.

Antioxidants are sulphites or metabisulphites such as potassium metabisulphite, or ascorbic acid, butylhydroxytolue-ne, butylhydroxyanisole or tocopherol.

Agents which impart protection against light are, for example, novantisolic acid.

Examples of tackifiers are cellulose derivatives, starch derivatives, polyacrylates, natural polymers such as alginates, and gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and if appropriate further auxiliaries, such as colorants, resorption acclerators, preservatives, antioxidants, agents which impart protection against light or viscosity-increasing substances.

The following may be mentioned as the hydrophobic phase (oils): paraffin oils, silicone oils, natural vegetable oils such as sesame oil, almond oil or castor oil, synthetic triglycerides such as caprylic/capric acid bi-gylcerides, triglyceride mixture with vegetable fatty acids of chain length $C_{8-12}$ or other specifically selected natural fatty acids, mixtures of partial glycerides or saturated or unsaturated, possibly also hydroxyl-containing, fatty acids, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid of medium chain length with saturated fatty alcohols of chain length $C_{16}-C_{18}$, isopropyl myristate, isopropyl palmitate, caprylic/capric esters of saturated fatty alcohols of chain length $C_{12}-C_{18}$, isopropyl stearate, oleyl oleate, decyl oleate, ethyl oleate, ethyl lactate, waxy fatty acid esters such as synthetic duck uropygial gland fat, dibutyl phthalate, diisopropyl adipate, mixtures of esters related to the latter, and others.

Fatty alcohols such as isotridecyl alcohol, 2-octyl-dodecanol, cetylstearyl alcohol or oleyl alcohol.

Fatty acids such as, for example, oleic acid and its mixtures.

The following may be mentioned as the hydrophilic phase:

water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate or alkylphenol polyglycol ethers;

ampholytic surfactants such as disodium N-lauryl-β-iminodipropionate or lecithin;

anionic surfactants, such as sodium lauryl sulphate, fatty alcohol ether sulphates, or the monoethanolamine salt of mono/dialkylpolyglycol ether ortho-phosphoric ester;

cationic surfactants such as cetyltrimethylammonium chloride.

Other auxiliaries which may be mentioned are: substances which increase the viscosity and stabilize the emulsion such as carboxymethylcellulose, methylcellulose and other cellulose and starch derivatives, polyacrylates, alginates, gelatin, gum arabic, polyvinyl pyrrolidone, polyvinyl alcohol, copolymers of methyl vinyl ether and maleic anhydride, polyethylene glycols, waxes, colloidal silica, or mixtures of the listed substances.

Suspensions can be administered orally, dermally or as injections. They are prepared by suspending the active compound in a carrier liquid, if appropriate with the addition of other auxiliaries such as wetting agents, colorants, resorption accelerators, preservatives, antioxidants substances which impart protection against light.

Carrier liquids which may be mentioned are all homogeneous solvents and mixtures of solvents.

Wetting agents (dispersants) which may be mentioned are the surfactants mentioned further above.

Other auxiliaries which may mentioned are those indicated further above.

Semi-solid preparations can be administered orally or dermally. They are distinguished from the above-described suspensions and emulsions only by their higher viscosity.

To prepare solid preparations, the active compound is mixed with suitable carriers, if appropriate with the addition of auxiliaries, and the mixture is brought into the desired form.

Carriers which may be mentioned are all physiologically acceptable solid inert substances. Suitable carriers are inorganic and organic substances. Examples of inorganic substances are common salt, carbonates such as calcium carbonate, hydrogen carbonates, aluminium oxides, silicas, clays, precipitated or colloidal silicon dioxide or phosphates.

Examples of organic substances are sugars, cellulose, foodstuffs and animal feeds such as dried milk, animal meals, fine or coarse cereal meals, and starches.

Auxiliaries are preservatives, antioxidants and colorants which have already been listed further above.

Other suitable auxiliaries are lubricants and gliding agents, such as, for example, magnesium stearate, stearic acid, talc, bentonites, and disintegrants, such as starch or crosslinked polyvinylpyrrolidone, or binders, such as, for example, starch, gelatin or linear polyvinylpyrrolidone, and dry binders, such as microcrystalline cellulose.

In the preparations, the active compounds can also be present in mixtures with synergists or with other active compounds which act against pathogenic endoparasites. Examples of such active compounds are L-2,3,5,6-tetrahydro-6-phenyl-imidazothiazole, benzimidazole carbamates, praziquantel, pyrantel and febantel.

Ready-to-use preparations contain the active compound in concentrations of 10 ppm–20 per cent by weight, preferably 0.1–10 per cent by weight.

Preparations which are diluted before administration contain the active compound in concentrations of 0.5–90 per cent by weight, preferably 5 to 50 per cent by weight.

In general, it has proven advantageous to administer amounts of approximately 1 to approximately 100 mg of active compound per kg of body weight per day to achieve effective results.

EXAMPLE A

In vivo nematode test

*Trichostrongylus colubriformis* / sheep

Sheep which had been infected for experimental purposes with *Trichostrongylus colubriformis* were treated after the prepatency time of the parasite had elapsed. The active compounds were administered orally in the form of the pure active compound, in gelatine capsules.

The degree of effectiveness was determined by quantitatively counting the worms deposited with the faeces before and after the treatment.

A complete halt to egg excretion after the treatment signifies that the worms had been aborted or damaged to such an extent that they no longer produce eggs (effective dose).

The active compounds tested and the dose rates which produce results (effective dose) can be seen from the Table below.

| Active compound Example No. | Effective dose in mg/kg |
|---|---|
| 1 | 25 |
| 9 | 10 |

EXAMPLE B

In vivo nematode test

*Haemonchus contortus* / sheep

Sheep which had been infected for experimental purposes with *Maemonchus contortus* were treated after the prepatency time of the parasite had elapsed. The active compounds were administered orally in the form of the pure active compound, in gelatine capsules.

The degree of effectiveness was determined by quantitatively counting the worms deposited with the faeces before and after the treatment.

A complete halt to egg excretion after the treatment signifies that the worms had been aborted or damaged to such an extent that they no longer produce eggs (effective dose).

The active compounds tested and the dose rates which produce results (effective dose) can be seen from the Table below.

| Active compound Example No. | Effective dose in mg/kg |
|---|---|
| 1 | 5 |
| 8 | 5 |
| 9 | 25 |

PREPARATION EXAMPLES

Example 1

Preparation of 5-(4-chlorophenoxy)-3-(2-chlorophenyl)-1,3,4-oxadiazolin-2-one 14.9 g (0.05 mol) of 4-chlorophenyl 2-(2-chlorophenyl)-hyd-razinecarboxylate are added at room temperature to a solution of 5 g (0.05 mol) of phosgene in 50 ml of toluene, and the resulting solution is slowly heated to 100° C., the evolving vapors being condensed by means of a dry-ice condenser. When the boiling point is reached, the latter is replaced by a coil condenser and the reaction mixture is refluxed until the evolution of gas has ceased. The solution is now concentrated under reduced pressure, and the resulting residue is dissolved in 100 ml of methylene chloride. 5 g (0.05 mol) of triethylamine are added to this solution, and stirring is continued at room temperature for 12 hours. To dissolve the triethylamine hydrochloride which has precipitated, the mixture is stirred with 100 ml of water, and the organic phase is separated off and washed in succession with dilute hydrochloric acid and water. After drying (Na₂SO ) the mixture is evaporated to dryness in vacuo and under reduced pressure, and the residue is recrystallized from diisopropyl ether. Yield: 81% of theory, melting point 110° C.

The following compounds are prepared analogously to Example 1:

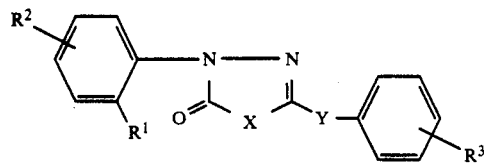

| Example No. | $R^1$ | $R^2$ | $R^3$ | X | Y | m.p. |
|---|---|---|---|---|---|---|
| 2 | H | 4-Br | H | O | O | 113° C. |
| 3 | H | 3-Cl | H | O | O | 76° C. |
| 4 | H | 4-Cl | 4-Cl | O | O | 112° C. |
| 5 | H | 3-Cl | 4-Cl | O | O | 106° C. |
| 6 | H | 4-Br | 4-Cl | O | O | 141° C. |
| 7 | Cl | H | 4-Br | O | O | 106° C. |
| 8 | CH₃ | 3-CH₃ | 4-Cl | O | O | 101° C. |
| 9 | F | 5-F | 4-Cl | O | O | 116° C. |
| 10 | H | 4-Cl | 4-Br | O | O | 122° C. |
| 11 | —Cl | —H | 4-CH₃ | O | O | 72° C. |
| 12 | —H | 3,5-(CH₃)₂ | —H | O | O | 103° C. |
| 13 | —H | 3 Cl, 4 F | —H | O | O | 96° C. |
| 14 | —H | 3,5-(CH₃)₂ | -4 Cl | O | O | 123° C. |

What is claimed is:

1. A substituted 1,3,4-thiadiazolinone of the formula

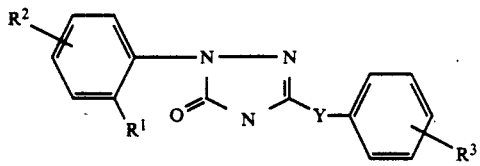

in which
$R^1$ represents halogen; or represents alkyl having 1 to 4 carbon atoms; alkoxy having 1 to 4 carbon atoms; alkylthio having 1 to 4 carbon atoms; halogenoalkyl having 1 to 4 carbon atoms and 1 to 5 halogen atoms, the halogen atoms being identical or different; halogenoalkoxy having 1 to 4 carbon atoms and 1 to 5 halogen atoms, the halogen atoms being identical or different; halogenoalkylthio having 1 to 4 carbon atoms and 1 to 5 halogen atoms, the halogen atoms being identical or different;
$R^2$ represent hydrogen; or represents alkyl having 1 to 4 carbon atoms; alkoxy having 1 to 4 carbon atoms; alkylthio having 1 to 4 carbon atoms; halogenoalkyl having 1 to 4 carbon atoms and 1 to 5 halogen atoms, the halogen atoms being identical or different; halogenoalkoxy having 1 to 4 carbon atoms and 1 to 5 halogen atoms, the halogen atoms being identical or different; halogenoalkylthio having 1 to 4 carbon atoms and 1 to 5 halogen atoms, the halogen atoms being identical or different; alkylenedioxy having 1 to 2 carbon toms; halogen-substituted alkylenedioxy having 1 to 2 carbon atoms and 1 to 4 halogen atoms, the halogen atoms being identical or different; halogen; cyano; nitro; dialkylamino having 1 to 4 carbon atoms per alkyl group; alkylcarbonyl having 2–4 carbon atoms; carbalkoxy having 2 to 4 carbon atoms; alkylsulphonyl having 1 to 4 carbon atoms; or represents phenyl, naphtha, phenoxy, naphthoxy, phenylthio or naphthylthio;
$R^3$ represents alkyl having 1 to 4 carbon atoms; alkoxy having 1 to 4 carbon atoms; alkylthio having 1 to 4 carbon atoms; halogenoalkyl having 1 to 4 carbon atoms and 1 to 5 halogen atoms, the halogen atoms being identical or different; halogenoalkoxy having 1 to 4 carbon atoms and 1 to 5 halogen atoms, the halogen atoms being identical or different; halogenoalkythio having 1 to 4 carbon atoms and 1 to 5 halogen atoms, the halogen atoms being identical or different; alkylenedioxy having 1 to 2 carbon atoms; halogen-substituted alkylenedioxy having 1 to 2 carbon atoms and 1 to 4 halogen atoms, the halogen atoms being identical or different; cyano; nitro; alkylcarbonyl having 2–4 carbon atoms; carbalkoxy having 2 to 4 carbon atoms; alkylsulphonyl having 1 to 4 carbon atoms; arylsulphonyl having 6 to 10 aryl carbon atoms; or represents phenyl, napthyl, phenoxy, naphthoxy, phenylthio or naphthylthio;
X represents S; and
Y represents O or S.

2. The substituted thiadiazolinone according to claim 1 in which
$R^1$ represents halogen, $C_1$-$C_4$-alkyl, $C_{1-4}$-alkoxy, $C_{1-4}$-halogenoalkoxy, or $C_{1-4}$-halogenoalkythio,
$R^1$ represents halogen, $C_1$-$C_4$-alkyl, $C_{1-4}$-alkoxy, $C_{1-4}$-halogenoalkoxy, $C_{1-4}$-halogenoalkylthio, or nitro or cyano; carbalkoxy; or alkylsulphonyl,
$R^3$ represents halogen, $C_{1-4}$-alkyl, $C_{1-4}$-alkoxy, $C_{1-4}$-halogenoalkoxy, $C_{1-4}$-halogenoalkylthio, or nitro or cyano; carbalkoxy; or alkylsulphonyl,
X represents S, and
Y represents O or S.

3. The substituted 1,3,4-thiadiazolinone of the formula

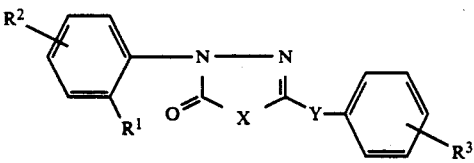

in which

| $R^1$ is | $R^2$ is | $R^3$ is | X is | Y is |
|---|---|---|---|---|
| —Cl | —H | —H | S | S |
| —H | 3,4-Cl₂ | -4-Cl | S | S |
| —CH₃ | -3-CH₃ | —H | S | S |
| —CH₃ | -3-CH₃ | -4-CH₃ | S | S |
| —Cl | -3-Cl | —H | S | S |
| —Cl | 6-Cl | —H | S | S |
| —F | —H | —H | S | S |
| —H | 4-Br | -4-Cl | S | S |
| —Cl | -3-Cl | -3-Cl | S | S |
| —Cl | -3-CH₃ | —H | S | O |
| —Cl | —H | —H | S | O |
| —CH₃ | -3-CH₃ | —H | S | O |
| —Cl | —H | -4-Cl | S | O |
| —CH₃ | —3CH₃ | -3-Cl | S | O |
| —F | 5-F | 4-Cl | S | O |
| —CH₃ | —CH₃ | 4-CH₃ | S | O |

-continued

| R¹ is | R² is | R³ is | X is | Y is |
|---|---|---|---|---|
| —Cl | —H | -4-CH₃ | S | O |
| —Cl | -4-CH₃ | -4-CH₃ | S | O |

4. A composition useful to combat endoparasites, which comprises a carrier and a substituted 1,3,4-thiadiazolinone according to claim 1 in an amount effective to combat endoparasites.

5. A method of combating endoparasites, which comprises administering to a patient a substituted according to claim 1 in an amount effective to combat endoparasites.

6. A method of combating endoparasites, which comprises administering to a patient a substituted 1,3,4-thiadiazolinone according to claim 3 in an amount effective to combat endoparasites.

* * * * *

UNITED STATES PATENT AND TRADEMARK OFFICE
CERTIFICATE OF CORRECTION

PATENT NO. : 5,093,343

DATED : March 3, 1992

INVENTOR(S) : Bonse et al.

It is certified that error appears in the above-identified patent and that said Letters Patent is hereby corrected as shown below:

Title Page      ABSTRACT: Line 3 delete " 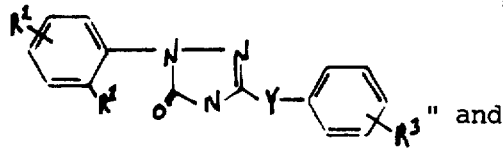 " and substitute -- 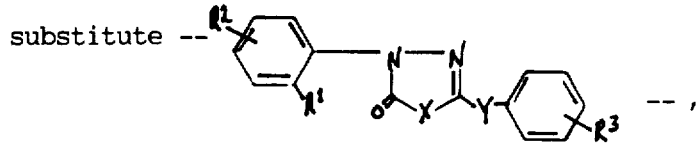 --, lines 9,17 delete " among " and substitute -- amongst --

Col. 1, line 25    Delete " 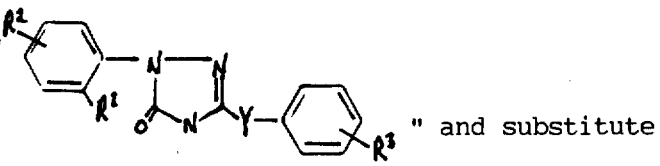 " and substitute

-- 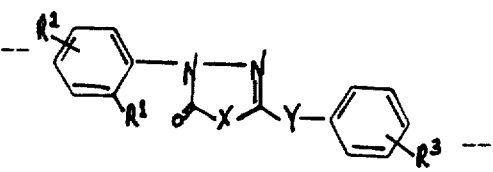 --

UNITED STATES PATENT AND TRADEMARK OFFICE
CERTIFICATE OF CORRECTION

PATENT NO. : 5,093,343

DATED : March 3, 1992

INVENTOR(S) : Bonse et al.

It is certified that error appears in the above-identified patent and that said Letters Patent is hereby corrected as shown below:

Col. 1, line 65    Delete " 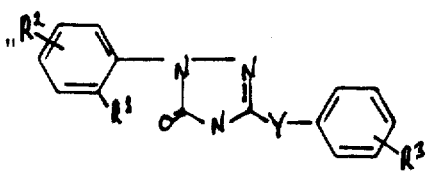 " and substitute

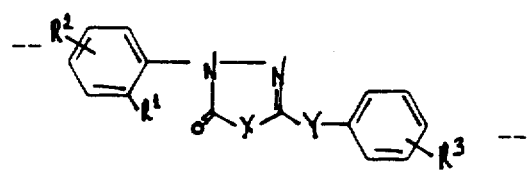 --

Col. 13, line 42    Delete " 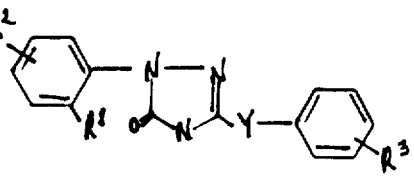 " and substitute

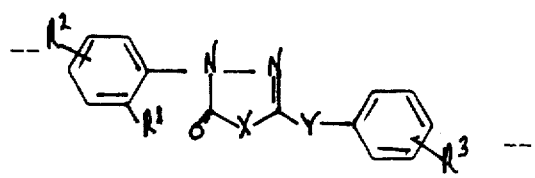 --

UNITED STATES PATENT AND TRADEMARK OFFICE
CERTIFICATE OF CORRECTION

PATENT NO. : 5,093,343

DATED : March 3, 1992

INVENTOR(S) : Bonse et al.

It is certified that error appears in the above-identified patent and that said Letters Patent is hereby corrected as shown below:

Col. 14, line 5    After " atoms; " insert -- arylsulphonyl having 6 or 10 aryl carbon atoms; --

Col. 14, line 6    Delete " naphtha " and substitute -- naphthyl --

Col. 14, line 29    After " substituted " insert -- 1,3,4- --

Col. 16, line 4,    After " substituted " insert -- 1,3,4-thiadiazolinone --

Signed and Sealed this

Nineteenth Day of October, 1993

Attest:

BRUCE LEHMAN

*Attesting Officer*    *Commissioner of Patents and Trademarks*